United States Patent
Suekane et al.

(10) Patent No.: US 7,034,199 B2
(45) Date of Patent: *Apr. 25, 2006

(54) ABSORBENT ARTICLE WITH BACK SHEET, AND METHOD FOR MANUFACTURING THE BACK SHEET

(75) Inventors: Makoto Suekane, Kagawa (JP); Toshio Inoue, Kagawa (JP); Shigeo Imai, Kagawa (JP)

(73) Assignee: Uni-Charm Corporation, Kawanoe (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/334,335

(22) Filed: Dec. 31, 2002

(65) Prior Publication Data

US 2003/0100875 A1    May 29, 2003

Related U.S. Application Data

(62) Division of application No. 09/740,640, filed on Dec. 19, 2000, now Pat. No. 6,531,204.

(30) Foreign Application Priority Data

Dec. 22, 1999    (JP)    ................. 11-364430

(51) Int. Cl.
*A61F 3/015*    (2006.01)
*B32B 27/012*    (2006.01)
*B32B 3/00*    (2006.01)

(52) U.S. Cl. .............. 604/358; 604/361; 442/394; 428/907.7; 428/156

(58) Field of Classification Search .............. 442/370, 442/378, 398, 394; 604/358, 361; 428/156, 428/172, 907.7, 409
See application file for complete search history.

(56) References Cited

U.S. PATENT DOCUMENTS

| | | | |
|---|---|---|---|
| 4,902,553 A | | 2/1990 | Hwang et al. |
| 5,820,618 A | * | 10/1998 | Roberts et al. ........ 604/385.04 |

FOREIGN PATENT DOCUMENTS

| | | |
|---|---|---|
| EP | 0 553 808 A1 | 8/1993 |
| EP | 0 776 645 A1 | 6/1997 |
| EP | 0 925 769 A2 | 6/1999 |
| JP | 05-168860 | 7/1993 |
| JP | 05-505149 A1 | 8/1993 |
| JP | 08-281795 A1 | 10/1996 |
| JP | 11-349702 | 12/1999 |
| WO | WO-99/16400 A1 | 4/1999 |

OTHER PUBLICATIONS

Patent Abstracts of Japan, JP 10 085257 A, Kao Corp., Apr. 1998, Abstract.

* cited by examiner

*Primary Examiner*—Terrel Morris
*Assistant Examiner*—Lynda Salvatore
(74) *Attorney, Agent, or Firm*—Darby & Darby

(57) ABSTRACT

There is disclosed an absorbent article including: a liquid-permeable top sheet; a back sheet; and an absorbent core sandwiched between the top sheet and back sheet. The back sheet is formed of a resin film containing an inorganic filler in a resin base material. The back sheet includes: a stretched moisture-permeable region; and a high optical transmittance region having a lower degree of orientation than that of the moisture-permeable region and/or left unstretched.

2 Claims, 9 Drawing Sheets

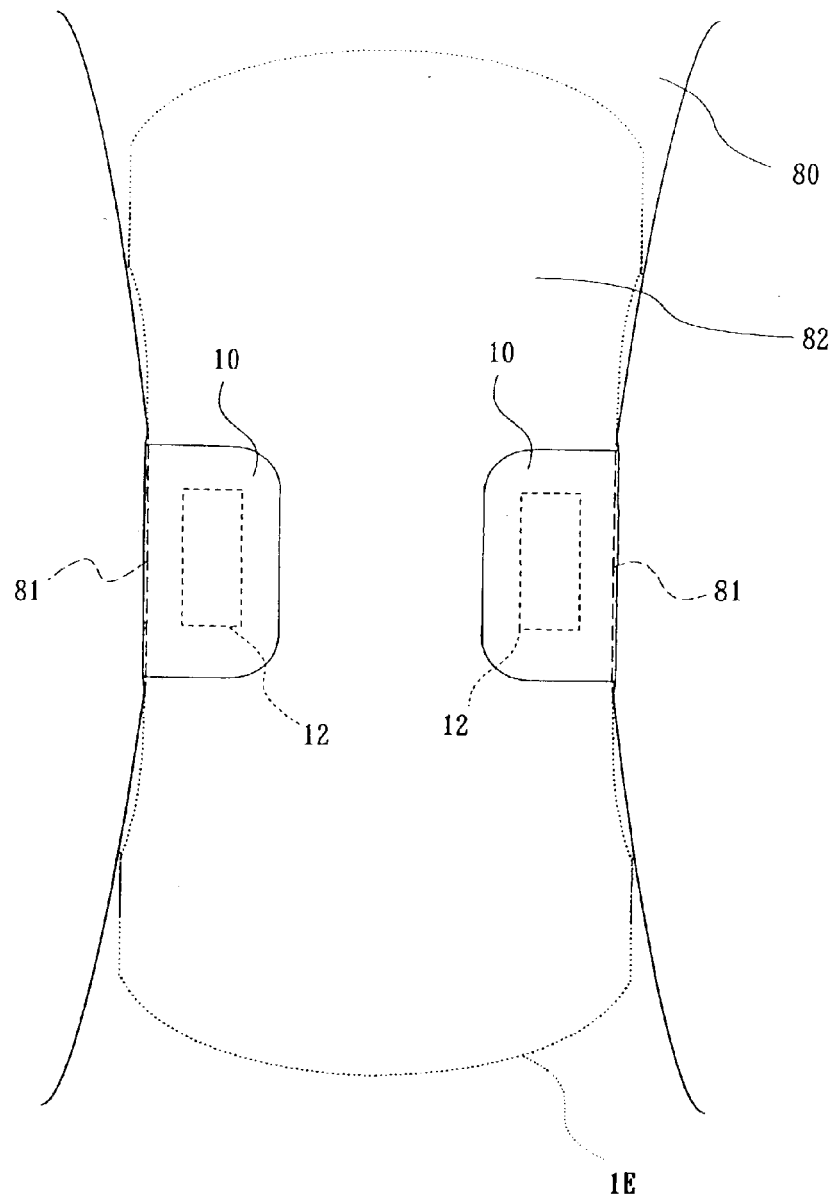

ABSORBENT ARTICLE WITH BACK SHEET, AND METHOD FOR MANUFACTURING THE BACK SHEET

This is a divisional of application Ser. No. 09/740,640, now U.S. Pat. No. 6,531,204, filed Dec. 19, 2000. The prior application is hereby incorporated herein by reference, in its entirety.

BACKGROUND OF THE INVENTION

1. Field of the Invention

The present invention relates to an absorbent article such as a disposable diaper, a sanitary napkin, a pantie liner or a urine absorbing pad and, more particularly, to an absorbent article using a back sheet having regions, which are different in the degree of orientation, and a method for manufacturing the back sheet.

2. Related Art

In order to absorb discharges, there have been recently employed a number of absorbent articles such as disposable diapers, sanitary napkins, pantie liners or urine absorbing pads. When a discharge is made while the absorbent article is worn, the absorbent article having absorbed the discharge is disposed of and is replaced by a new one.

Here, the back sheet to be ordinarily employed in the absorbent article is exemplified by a liquid-impermeable resin sheet. The back sheet is formed by stretching a resin film containing an inorganic filler so as to enhance the air-permeability and the moisture-permeability so that the back sheet is made opaque. In the case of the diaper, therefore, in order to confirm whether or not the wearer has made a discharge, the care taker has to remove the diaper from the wearer to confirm the inside of the diaper. This is a seriously troublesome work for the care taker.

In Unexamined Published Japanese Patent Application No. 5-168660, therefore, there is disclosed a uniaxially oriented air-permeable film which is embossed to have a moisture-permeability of 1,000 g/m$^2$/24 hrs or more so as to enhance the optical transmittance. In this film, however, the moisture-permeability is not so lowered that the optical transmittance cannot be enhanced so high.

In Unexamined Published Japanese Patent Application No. 10-85257, on the other hand, there is disclosed a back sheet of a developing type disposable diaper. In this back sheet, a see-through portion is formed in at least a central portion in the longitudinal direction. This back sheet is formed like before of a porous sheet, which is prepared by stretching the resin film containing the inorganic filler, for enhancing the moisture-permeability. In the see-through portion, a transparent portion is formed by crushing the pores of the porous sheet by an embossing treatment thereby to eliminate the scattering of light. If the porous sheet is further embossed, however, pin holes will be easily formed, because the embossed portion is lowered in its strength. There is also a description that the transparent portion could be formed by applying wax, varnish or hot melt in place of the embossing treatment. However, the applied material will ooze or stick on the film surface and requires a drying treatment after applied, so that the cost for the material and for the treatment rises.

Thus in the disposable diaper, there has been demanded a back sheet which is so enhanced in the optical transmittance that whether or not the discharge has been made can be confirmed from the outside without lowering the air-permeability, the moisture-permeability or the strength.

Here will be described a sanitary napkin. This sanitary napkin may be provided on the two longitudinally extending sides with wings which extend in the width direction. When the sanitary napkin is worn, the wings are folded back to the lower side of the crotch portion of the underwear such as panties so that the edge portions of the panties can be prevented from being blotted with the discharge. Moreover, the napkin can be prevented from going out of position by adhesion means disposed on the wings for attaching the napkin to the panties. These wings are formed by protruding the member constructing the body of the napkin, such as the adhered back sheet and top sheet, in the width direction from the two side portions of the body of the napkin.

In the back sheet of the sanitary napkin, however, the back sheet is formed as in the diaper by stretching the film so as to enhance the air-permeability so that the optical transmittance is extremely lowered. When the panties wearing the napkin with the wings is seen from the outside, therefore, the presence of the wing portions, i.e., the wearing of the napkin is apparent from the outside. Only the wings could be made of a material different from that of the back sheet, such as a high optical transmittance sheet so that the wearing of the napkin could not be confirmed in the appearance. However, this makes the manufacture process complex to raise the cost.

Thus, the absorbent article has been desired to have a partially high optical transmittance. However, the portion desired to have a high optical transmittance is different among the kinds of absorbent articles.

SUMMARY OF THE INVENTION

An object of the invention is to provide an absorbent article using a back sheet which has a high optical transmittance portion and an air- and moisture-permeable portion.

Another object of the invention is to provide a method for manufacturing the back sheet.

According to an aspect of the invention, there is provided an absorbent article comprising: a liquid-permeable top sheet; a back sheet; and an absorbent core sandwiched between the top sheet and back sheet, wherein the back sheet is formed of a resin film containing an inorganic filler in a resin base material, and wherein the back sheet includes: (a) a stretched moisture-permeable region; and (b) a high optical transmittance region having a lower degree of orientation than that of the moisture-permeable region and/or left unstretched.

In the absorbent article of the invention, there are formed in one back sheet the high optical transmittance region and the high air- and moisture-permeable region. As a result, the high optical transmittance region can be formed in a portion of the absorbent article while the air-permeability and the moisture-permeability being retained in the entire absorbent article. In the diaper, for example, whether or not the discharge has been made can be confirmed from the outside of the diaper being worn. In the sanitary napkin, the presence of the wings cannot be seen from the outside of the panties. Moreover, this strength of the back sheet is hard to degrade.

The resin base material is preferably a polyolefin resin.

The mixing ratio between the resin base material and the inorganic filler is preferably 20 to 70% by mass: 80 to 30% by mass.

In the case where the absorbent article is a disposable diaper, the high optical transmittance region (b) is preferably positioned to cover the entirety or a portion of the back of the absorbent core. In this case, furthermore, the high optical transmittance region (b) is preferably provided in the generally widthwise central portion of the region having the absorbent core and in the region containing the widthwise center of the absorbent core and having one quarter of the width size of the diaper, and/or in the generally longitudinal central portion of the region having the absorbent core and in the region containing the longitudinal center of the absorbent core and having one quarter of the longitudinal size of the diaper.

It should be noted that: the term "longitudinal central portion/region" as used herein means the intermediate portion/region located between two end regions lying opposite one another in the longitudinal direction; the term "widthwise central portion/region" as used herein means the intermediate portion/region located between two side regions lying opposite one another in the widthwise direction. It should be also noted that: the term "longitudinal center" as used herein means the midpoint located between two end edges lying opposite one another in the longitudinal direction; the term "widthwise center" as used herein means the midpoint located between two side edges lying opposite one another in the widthwise direction.

In the case where the absorbent article is a sanitary napkin including a pair of wing portions disposed on the two sides of the region of the absorbent core and extending outwardly in the widthwise direction, on the other hand, the moisture-permeable region (a) is preferably positioned to cover the entirety or a portion of the back of the absorbent core whereas the high optical transmittance region (b) is preferably positioned in at least the wing portions. In this case, furthermore, the moisture-permeable region (a) is preferably positioned in the generally widthwise central portion of the region having the absorbent core and over one half or more of the width size of the absorbent core, and/or in the generally longitudinal central portion of the region having the absorbent core and over one half or more of the longitudinal size of the absorbent core.

The moisture-permeable region (a) is preferred to have a moisture-permeability of 1,000 g/m²·24 hrs or more.

The moisture-permeable region (a) is preferred to have a total optical transmittance of 50% or less according to JIS-K-7105.

The high optical transmittance region (b) is preferred to have a total optical transmittance of 60% or more according to JIS-K-7105.

If the back sheet in the moisture-permeable regions (a) has a thickness T1 and if the back sheet in the high optical transmittance region (b) has a thickness T2, it is preferred that the values T1 and T2 satisfy the following Formulas:

$$20 \leq \{(T2-T1)/T1\} \times 100 \leq 30.$$

The back sheet may have a multi-layered structure in at least the high optical transmittance region (b).

The back sheet to be used in the absorbent article of the invention can be formed simply at a low cost. According to another aspect of the invention, there is provided a method for manufacturing a back sheet for an absorbent article including: a liquid-permeable top sheet; the back sheet; and an absorbent core sandwiched between the top sheet and back sheet. A film containing an inorganic filler in a resin base material is partially stretched to form: (a) a stretched moisture-permeable region; and (b) a high optical transmittance region having a lower degree of orientation than that of the moisture-permeable region and/or left unstretched.

In the above, a film being continuously fed may be stretched exclusively at a central portion in a width direction (or in CD) thereof to form the moisture-permeable region (a) at the central portion.

In an alternative, a film being continuously fed may be stretched exclusively on two side portions in a width direction (or in CD) thereof to form the moisture-permeable regions (a) on the two side portions.

In another alternative, a film being continuously fed may be partially stretched at a predetermined interval in a longitudinal direction (or in MD) thereof to form the moisture-permeable regions (a) at a spacing in the longitudinal direction.

In still another alternative, a film being continuously fed may be partially stretched at a predetermined interval in a width direction (or in CD) thereof to form the moisture-permeable regions (a) at a spacing in the width direction.

The film may be stretched by an embossing treatment to form the moisture-permeable region (a).

It is possible that a film having partially different thicknesses is formed of a material containing the inorganic filler in the resin base material and is stretched to form the moisture-permeable region (a) in the thinner portion and the high optical transmittance region (b) in the thicker portion.

It is also possible that an unstretched film is partially coated with a transparent film and is then stretched to form the moisture-permeable region (a) in the portion, which is not coated with the transparent film, and the high optical transmittance region (b) in the portion which is coated with the transparent film.

BRIEF DESCRIPTION OF THE DRAWINGS

FIG. 9 is a top plan view of a portion showing a state in which the sanitary napkin shown in FIG. 7 is attached to panties.

DESCRIPTION OF THE PREFERRED EMBODIMENTS

Figure 1:
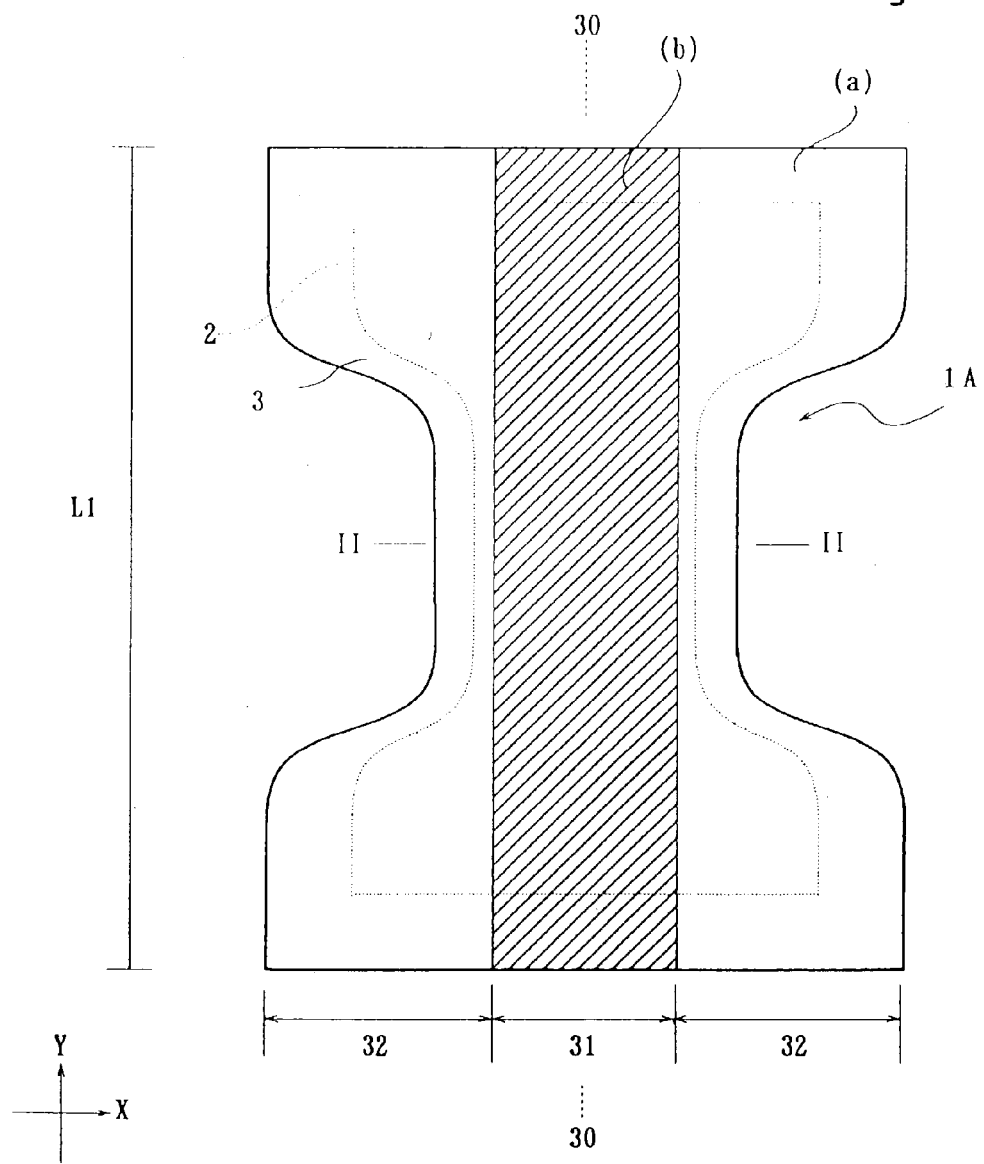
FIG. 1 is a top plan view, as taken from the back side, of a diaper as an absorbent article according to one embodiment of the invention.
Figure 2:
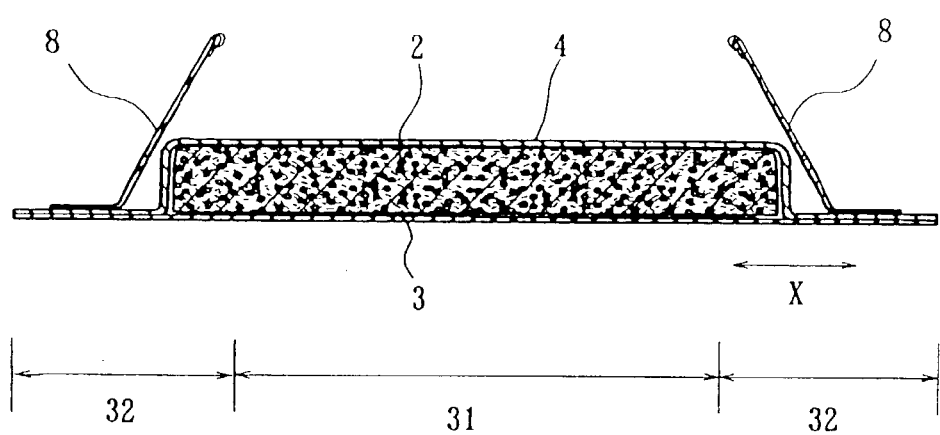
FIG. 2 is a section taken along line II—II of the diaper shown in FIG. 1.

FIG. 1 is a top plan view, as taken from the back side, of a diaper as an absorbent article according to one embodiment of the invention, and FIG. 2 is a section taken along line II—II of the diaper shown in FIG. 1. Here, the longitudinal direction of the diaper is taken in a Y-direction, and the widthwise direction generally perpendicular to the Y-direction is taken in an X-direction.

A disposable diaper 1A, as shown in FIG. 1, is the so-called "open type" diaper and is constructed, as shown in FIG. 2, to include: a liquid-permeable top sheet 4 to confront the wearer; a liquid-impermeable back sheet 3; and an absorbent core 2 sandwiched between the top sheet 4 and the back sheet 3. These top sheet 4, back sheet 3 and absorbent core 2 are individually formed into the hour glass shape. However, the absorbent core 2 may have a rectangular shape. The top sheet 4 and the back sheet 3 are adhered and jointed to each other at the outer sides of the absorbent core 2 in the X-direction and in the Y-direction by means of a hot-melt type adhesive, for example.

For example, the top sheet 4 is made of nonwoven fabric comprising hydrophobic fibers subjected to a hydrophilic treatment or hydrophilic fibers, such as point bond, air-through, spun bond or spun lace nonwoven fabric. The top sheet 4 has a basis weight (this may be referred to as "METSUKE") of 10 to 40 $g/m^2$. Moreover, the top sheet 4 may be formed by laying a cushion layer of bulky nonwoven fabric over the former nonwoven fabric. On the other hand, the absorbent core 2 is formed of an absorbent material, for example, pulverized pulp or a mixture of pulverized pulp and a highly water-absorbing polymer, which is enveloped with an absorbent sheet of tissues.

On the other hand, the diaper 1A may be provided with leg cuffs for ensuring the close contact around the legs, although not shown, and leakage preventing cuffs 8 for preventing sideway leakage, as shown in FIG. 2.

The liquid-impermeable back sheet 3 is made of a resin sheet which is prepared by orientating a resin film containing an inorganic filler to have regions different in the degree of orientation. In order to reduce the uncomfortableness of the wearer, the diaper 1A may be provided with a nonwoven fabric layer on the outer side (i.e., on the lower side of the back sheet 3, as seen in FIG. 2) of the back sheet 3 (of the resin sheet). In this modification, the nonwoven fabric to be employed has a high moisture-permeability and a high optical transmittance so as not to impair the functions of regions (a) and (b), which will be described hereinbelow, of the back sheet 3 (of the resin sheet).

This back sheet 3 is different in properties between its widthwise central region 31 containing the center line 30 of the diaper 1A and its two adjoining side regions 32 and 32. Specifically, these two side regions 32 and 32 are moisture-permeable regions (a) having a relatively high moisture-permeability, whereas the central region 31 is a region (b) (as hatched in FIG. 1) having a higher optical transmittance than the moisture-permeable regions (a).

When the wearer of the diaper 1A makes a discharge, this discharge is absorbed mainly at the widthwise central region 31 of the absorbent core 2 of the diaper 1A. Since this central region 31 has the high optical transmittance, the discharge can be discriminated in its color, when absorbed by the absorbent core 2, from the outside of the diaper 1A through the back sheet 3. Thus, it can be easily confirmed whether or not the wearer has discharged.

At this region (b) of the high optical transmittance, the resin sheet constituting the back sheet 3 is formed by either not orientating the film or orientating the film at a low degree of orientation. In the region (b), therefore, the optical transmittance is kept so high or not degraded as can confirm the color of the discharge which was absorbed by the absorbent core 2. The region (b) is preferred to have a total optical transmittance of 60% or more according to JIS-K-7105. This standard is preferably satisfied even when the nonwoven fabric layer is laminated on the outer side of the resin sheet. Here, the region (b) has a low moisture-permeability because it has few pores.

At the two side regions 32 and 32, on the other hand, the resin sheet is formed by orientating the film at a higher degree of orientation than that of the region (b) so that the optical transmittance is lower than that of the region (b) whereas the moisture-permeability is made higher in the presence of the pores. Even with the region (b) of the low moisture-permeability being present in the central region 31, therefore, the inside of the diaper 1A does not become stuffy so that the wearer does not have a rash. For this effect, the moisture-permeable regions (a) are preferred to have a moisture-permeability of 1,000 $g/m^2 \cdot 24$ hrs or more. This standard is preferably satisfied even when the nonwoven fabric layer is laminated on the outer side of the resin sheet.

The moisture-permeability is measured by the following method (according to JIS Z-0208).

(1) 20 ml of water is poured into a cup having a radius of 0.03 m.

(2) The cup is put in a cup-shaped bed a size larger than the cup, and the cup-shaped bed is covered at its mouth with a film, the moisture-permeability of which is to be measured. Then, the edge of the film and the edge of the cup-shaped bed are sealed up with heated wax (e.g., a mixture of (yellow) beeswax and (white) paraffin at 6:4). Thus, a sample is obtained.

(3) This sample is allowed to stand for 24 hrs in a constant temperature/moisture apparatus (at 20° C. and 60% RH), and the weight of the sample is then measured (to have a value A).

(4) The sample is allowed to stand for 24 hrs in a constant temperature/moisture apparatus (at 40° C. and 60% RH) and then for 30 minutes in a constant temperature/moisture apparatus (at 20° C. and 60% RH), and the weight of the sample is measured (to have a value B).

The moisture-permeability is calculated from the following Formula by applying the values A and B obtained:

$$\text{Moisture-Permeability } (g/m^2 \cdot 24 \ hrs) = (B-A)/(\pi \times 0.03 \times 0.03).$$

When the absorbent article of the invention is exemplified by the diaper 1A shown in FIG. 1, the width size of the region (b) (or the central region 31) in the X-direction is preferred to be within about 30 to 70% of the entire width of the film. With the region (b) being formed over such range, the discharge can be reliably recognized. In addition, the diaper 1A hardly becomes stuffy in its inside.

Any resin base material for the resin sheet can be employed, but a polyolefin resin is preferably used for the aspects of cost and safety.

As this polyolefin resin, there can be enumerated polypropylene, low-density polyethylene (LDPE), high-density polyethylene, linear low-density polyethylene (LLDPE), polybutene, ethylene-propylene copolymer, ethylene-butene copolymer and ethylene-vinylacetate copolymer. At least one kind of these can be employed. Of these, the preferable one is the LDPE, and the more preferable one is the LLDPE.

As the inorganic filler, there can be enumerated barium sulfate, barium carbonate, calcium sulfate, calcium carbonate, magnesium hydroxide, magnesium oxide, aluminum hydroxide, zinc oxide, titanium oxide, silica and talc. Of these, barium sulfate, calcium carbonate and magnesium hydroxide are preferable. To the resin, there can be added an ultraviolet ray absorbent, an oxidation inhibitor, an stabilizer, a coloring agent, a lubricant and so on.

The mixing ratio between the resin base material and the inorganic filler is preferably 20 to 70% by mass: 80 to 30% by mass. If the inorganic filler is more than the upper limit, the resin film becomes clouded in white before oriented so that it cannot form the region (b) having the high optical transmittance. If the inorganic filler is less than the lower limit, on the other hand, pin holes are formed when the resin film is oriented. More preferably, the ratio of the inorganic filler is 60 to 30% by mass.

The polyolefin resin and inorganic filler thus far specified and, optionally, other additives are mixed by using a Henschel mixer, a super mixer, a tumbler type mixer or the like and is kneaded into pellets by the ordinary single- or double-screw extruder. Next, after another pelletized polyolefin resin is added, if necessary, those pellets are melted at a melting point or higher of the base resin, preferably at a temperature higher than the melting point+20° C. and lower than the decomposition temperature, and filmed into a resin film by using a inflation molding machine or a T-die molding machine. At this time, the material may be directly filmed by the extruder without being pelletized. This resin film preferably has a thickness of 10 to 90 μm (microns). Under the above-specified lower limit, the film is liable to break in the subsequent orientation. Over the upper limit, no special problem arises, but the productivity is slightly lowered.

The resin film thus prepared is oriented in at least one direction by the well-known method such as the roll method or the tender method to produce a resin sheet having the moisture-permeable regions (a) of the high moisture-permeability and the region (b) of the high optical transmittance. The orientation is preferably uniaxial orientation in the X-direction (CD: Cross Direction) of 1.1 to 2.5 times.

Figure 3A:
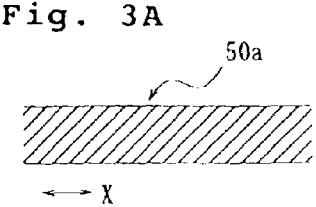
FIGS. 3A, 3B and 3D are sections of a portion of a film before oriented.
Figure 3B:
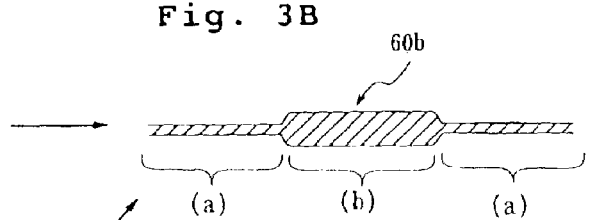

In order to prepare the resin sheets having the regions (a) and (b), for example, a film 50*a* having a uniform thickness, as shown in FIG. 3A, is partially stretched to form a resin sheet 60*b*, as shown in FIG. 3B. In this resin sheet 60*b*, there are formed: the moisture-permeable regions (a) of the high moisture-permeability which were stretched to a smaller thickness; and the high optical transmittance region (b) which substantially retains the thickness of the resin sheet 50*a* before stretched. Here, the film 50*a* before stretched is preferable to have a basis weight of 20 to 40 g/m$^2$.

Figure 3C:
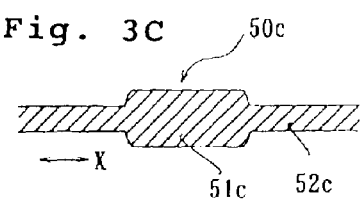
FIGS. 3C and 3E are sections of a portion of a resin sheet after oriented.

In an alternative, as the film to be stretched, use can be made of a film 50*c* having a thicker portion 51*c* and thinner portions 52*c* as shown in FIG. 3C, which is formed by a corrugated die in the formation of the film. This film 50*c* may be stretched in its entirety to form the resin sheet 60*b*, as shown in FIG. 3B. Even if the film 50*c* is stretched in its entirety, the thicker portion 51*c* is not changed in its substantial thickness, so that its optical transmittance is not lowered. On the other hand, the thinner portions 52*c* are sufficiently stretched to form the moisture-permeable regions (a) of the high moisture-permeability. Here, the film 50*c* before stretched is preferred to have a basis weight of 40 to 50 g/m$^2$ in its entirety.

Figure 3D:
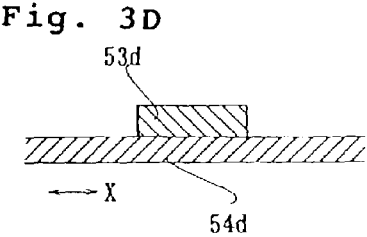
Figure 3E:
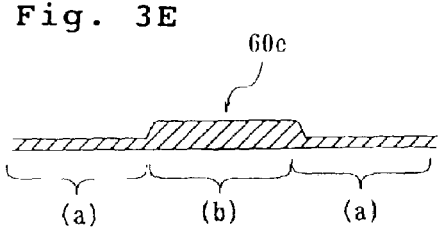

In another alternative, the resin sheet may be formed such that: a film (or resin) 53*d* is laid over a portion of a film 54*d* having a uniform thickness, as shown in FIG. 3D; and the film 54*d* is then stretched like that shown in FIG. 3C to form a resin sheet 60*e*, as shown in FIG. 3E. At this time, the portion laminated with the film 53*d* provides the high optical transmittance region (b) in the resin sheet 60*e*. It is preferable to employ a transparent film having a high optical transmittance as the film 53*d*.

Here, in order to develop the different functions in the regions (a) and the region (b), the orientation is preferably performed such that the values T1 and T2 satisfy the following Formulas, if the resin sheet in the high moisture-permeable regions (a) has a thickness T1 and if the resin sheet in the high optical transmittance region (b) has a thickness T2:

$$20 \leq \{(T2-T1)/T1\} \times 100 \leq 30.$$

The aforementioned orientation may be performed separately at multiple stages or in two or more directions including the X-direction and the Y-direction. The biaxial orientations are preferred to be simultaneously made. These biaxial orientations enhance the strength of the resin sheet.

The following embossing treatment can be additionally enumerated as the means for forming the regions (a) and the region (b) by making the degree of orientation partially different in the resin film.

Figure 4A:
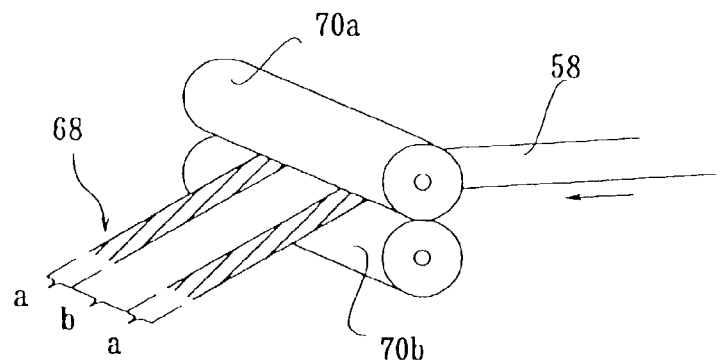
FIG. 4A is a perspective view for explaining a state in which the film is embossed.
Figure 4B:
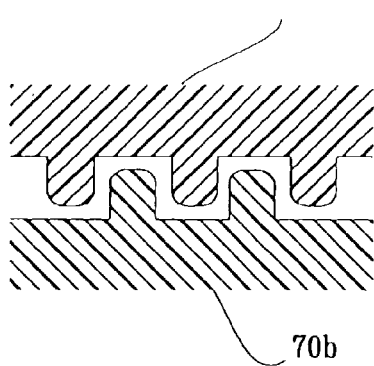
FIG. 4B is a section of a portion of embossing rolls.

In FIG. 4A, a similar film 58, as continuously fed, is pinched by embossing rolls 70*a* and 70*b* so that it is pressed and stretched to form a resin sheet 68 having the regions (a) and the region (b). The embossing rolls 70*a* and 70*b* are corrugated, in FIG. 4B, in the surfaces of their two side regions. The film 58 is pinched and pressed by those corrugations so that it is stretched to form the regions (a).

When the film is embossed while being heated, however, the pin holes are liable to be formed in the film. Moreover, since the film is shrunken if embossed in the heated state, there arises another problem that the film size is liable to warp. When the orientation is made by the embossing treatment, therefore, care should be taken to hold the degree of orientation by considering those problems.

Thus, the back sheet having the high moisture-permeable regions (a) and the high optical transmittance region (b) in the invention can be manufactured simply and at a low cost from one material (i.e., one film). Unlike the case in which the back sheet is formed as in the prior art by partially mounting members of a different material, on the other hand, a series of works from the formation of the back sheet to the completion of the absorbent article can be performed by carrying the film orienting step on the assembly line of the absorbent article.

Figure 5:
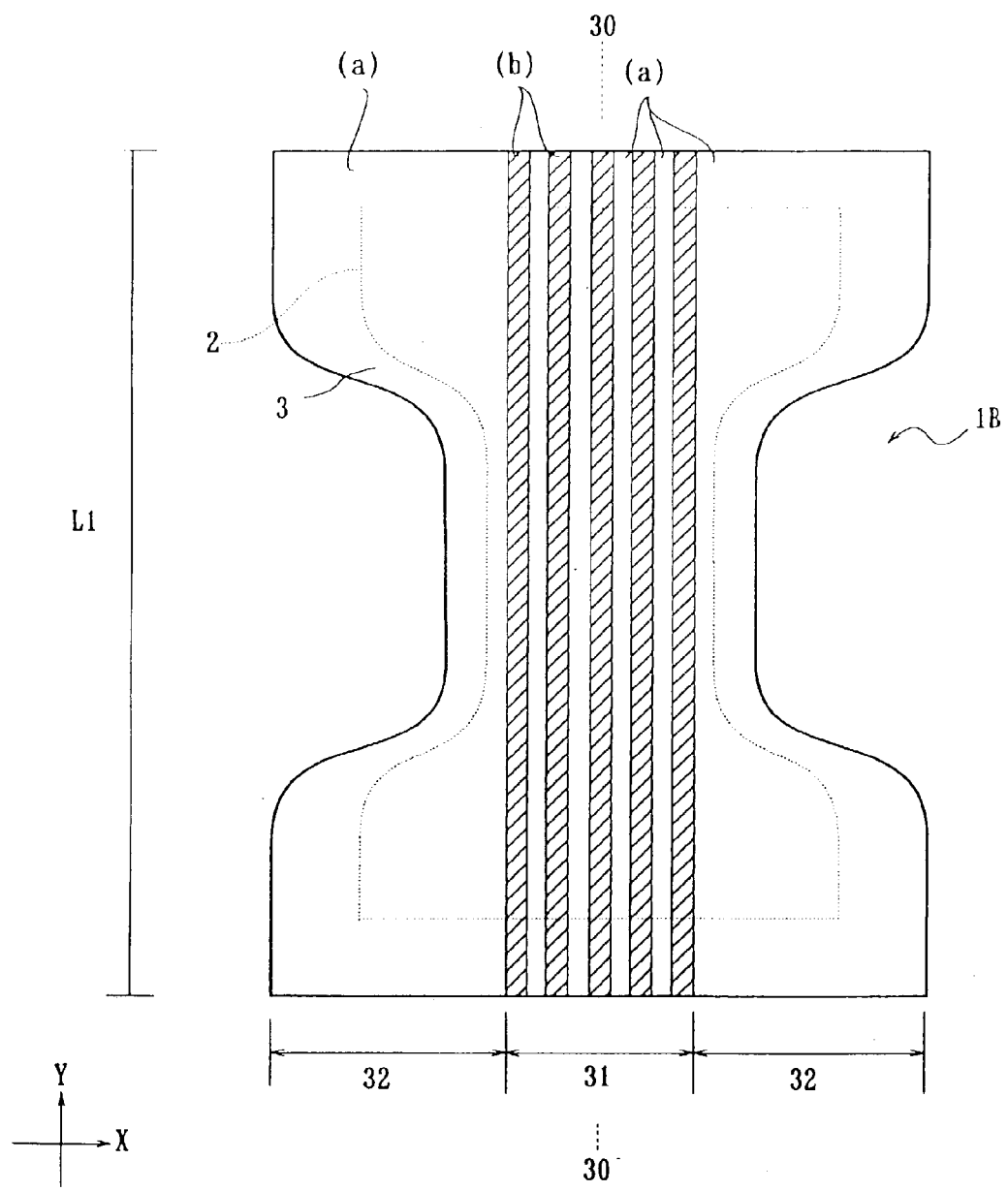
FIG. 5 is a top plan view, as taken from the back side, of a diaper according to another embodiment of the invention.
Figure 6:
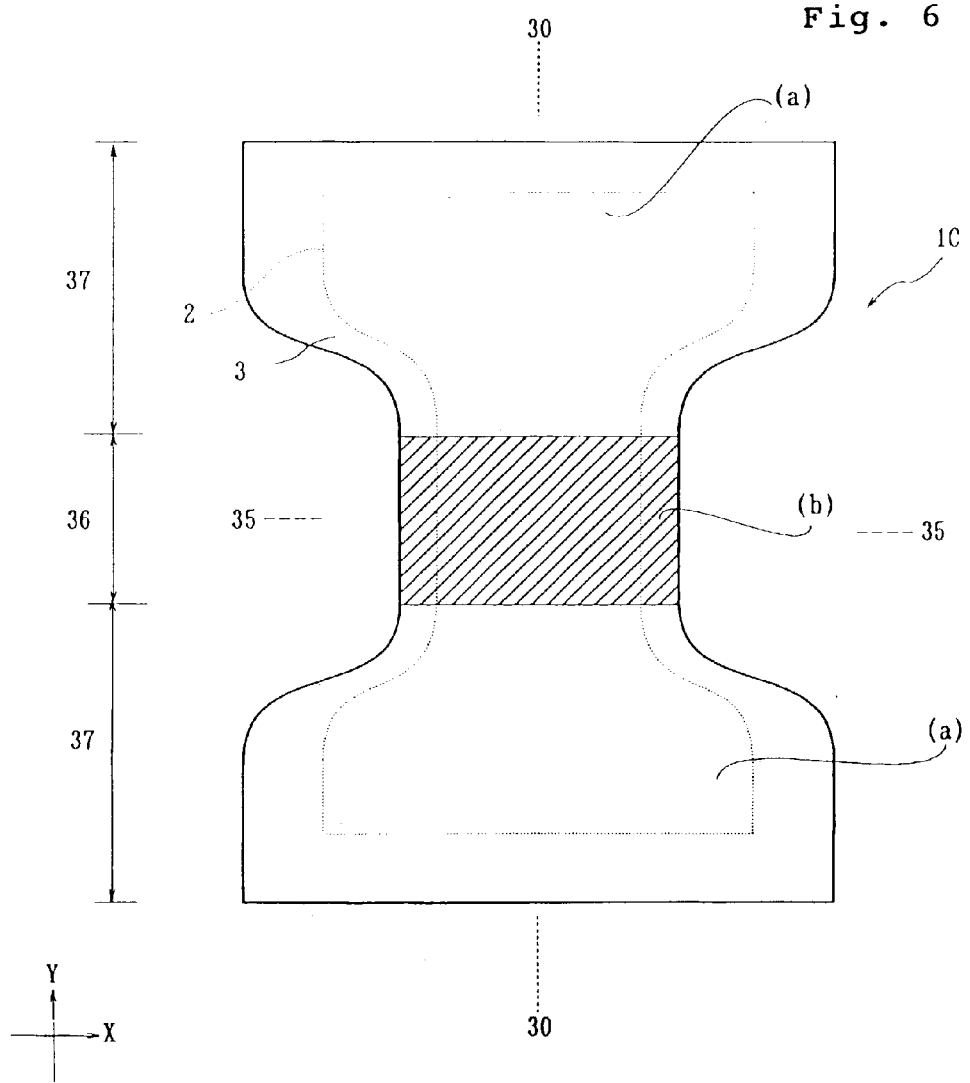
FIG. 6 is a top plan view, as taken from the back side, of a diaper according to still another embodiment of the invention.

FIG. 5 is a top plan view, as taken from the back side, of a diaper of another embodiment of the invention, and FIG. 6 is a top plan view, as taken from the back side, of a diaper of still another embodiment of the invention.

In a diaper 1B shown in FIG. 5, there are formed in the widthwise central region 31 of the diaper a plurality of high optical transmittance regions (b) which are continuously extended in the Y-direction at a predetermined spacing in the X-direction from each other. In the central region 31, the regions (a) are formed between the regions (b) extending in the Y-direction. Therefore, the diaper 1B not only can reliably recognize whether or not the discharge has been made, like the diaper 1A shown in FIG. 1, but also has a higher moisture-permeability in its entirety than that of the diaper 1A. When the regions (a) are thus formed in the stripe shape, they may be arranged alternately with the regions (b) all over the surface of the back sheet 3.

In a diaper 1C shown in FIG. 6, on the other hand, unlike the foregoing diapers 1A and 1B having the regions (b) throughout the whole length, the high optical transmittance region (b) is formed all over the width size in the X-direction of the diaper in the longitudinal central region 36 containing the center line 35 of the diaper. This resin sheet can be obtained by stretching the film, as fed in the MD, at a predetermined spacing in the MD. Alternatively, the diaper 1C may be manufactured by laminating the resin sheet, as can be prepared to have the high optical transmittance region (b) at the center region in the CD by the methods shown in FIGS. 3 to 4, over the absorbent core and the top sheet such that the MD may be in the X-direction.

In the case where the absorbent article is exemplified by the diaper, in order to confirm whether or not a discharge was made, reliably from the outside, it is preferable that the high optical transmittance region (b) is provided in the generally widthwise central portion of the region having the absorbent core 2 and in the region containing the widthwise center of the absorbent core and having one quarter of the width size of the diaper, and/or in the generally longitudinal central portion of the region having the absorbent core and in the region containing the longitudinal center of the absorbent core and having one quarter of the longitudinal size of the diaper.

Figure 7:
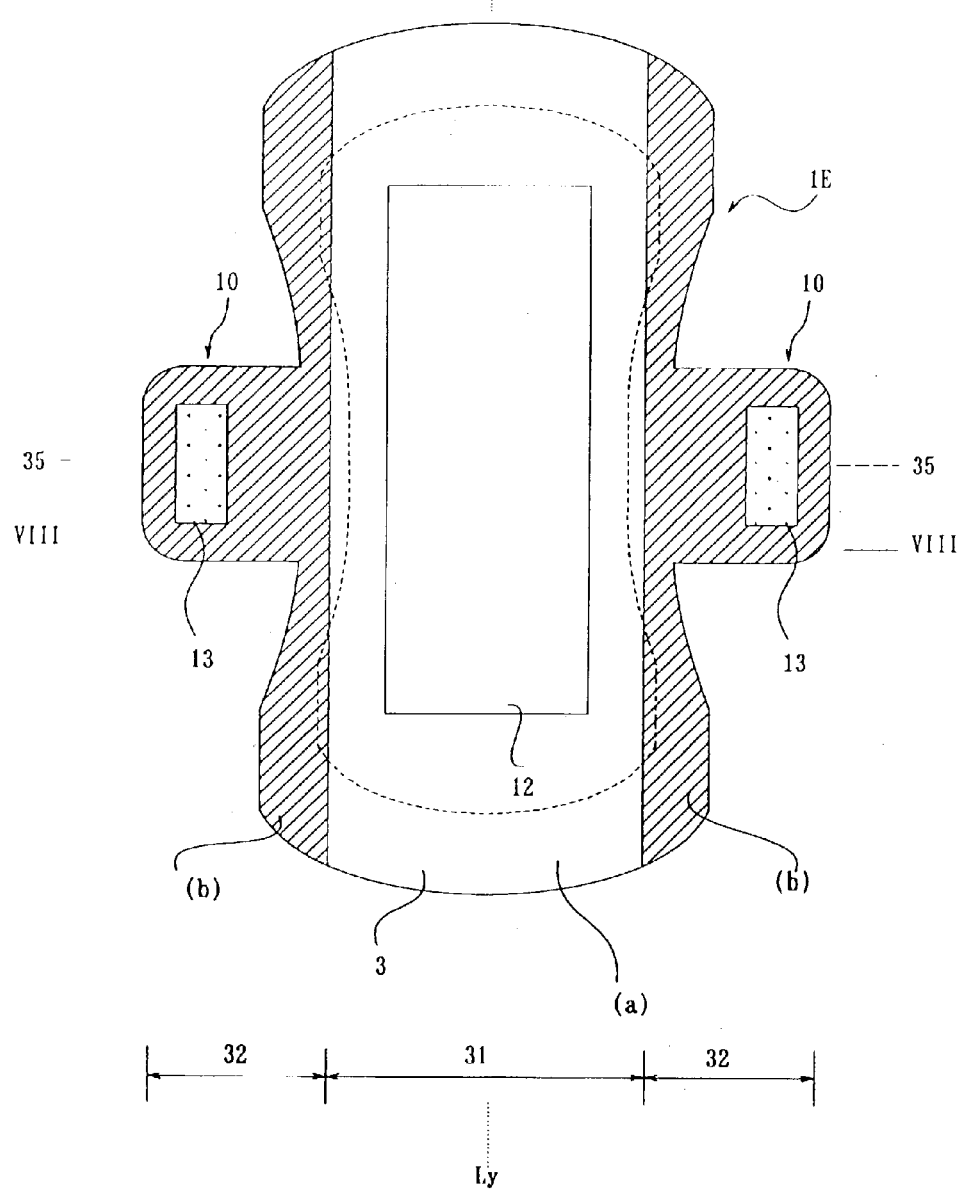
FIG. 7 is a top plan view, as taken from the back side, of a sanitary napkin as an absorbent article according to still another embodiment of the invention.
Figure 8:
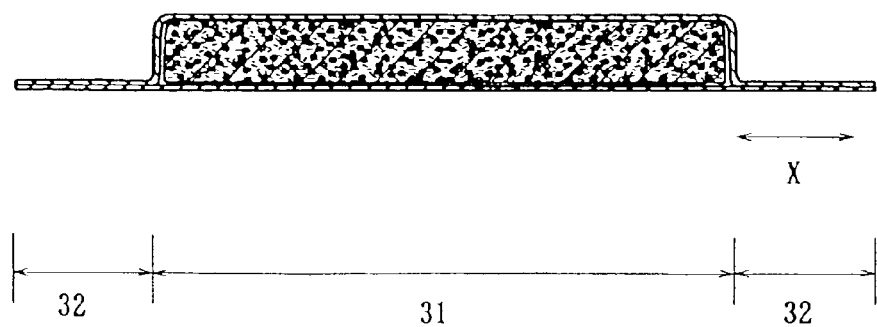
FIG. 8 is a section taken along line VIII—VIII of the sanitary napkin shown in FIG. 7.

FIG. 7 is a top plan view, as taken from the back side, of a sanitary napkin as an absorbent article according to still another embodiment of the invention; FIG. 8 is a section taken along line VIII—VIII of the sanitary napkin shown in FIG. 7; and FIG. 9 is a top plan view of a portion showing a state in which the sanitary napkin shown in FIG. 7 is attached to panties. Here, the longitudinal direction of the sanitary napkin or the absorbent article is taken like before in the Y-direction, and the widthwise direction generally perpendicular to the Y-direction is taken in the X-direction.

A sanitary napkin 1E, as shown in FIG. 7, is generally symmetric with respect to the center line Ly extending in the Y-direction. This sanitary napkin 1E is provided, as seen from the section shown in FIG. 8, with: a liquid-permeable top sheet 4 on the liquid receiving side; a liquid-impermeable back sheet 3 on the outer side; and an absorbent core 2 sandwiched between the top sheet 4 and the back sheet 3. These individual members are similar to those of the foregoing diapers. In the vicinity of the center line 35 located between two end edges lying opposite one another in the Y-direction of the sanitary napkin, moreover, the top sheet 4 and the back sheet 3 are individually extended in the X-direction to form wings 10 and 10.

As shown in FIG. 7, the sanitary napkin 1E is provided with an adhesive portion 12 on the back side of its body and adhesive portions 13 on the back sides of the wings 10. The sanitary napkin 1E is attached, when worn, to the crotch portion 82 on the inner side of panties 80, as shown in FIG. 9. At this time, the adhesive portion 12 on the back of the body is retained on the inner face of the crotch portion 82 of the panties 80. Then, the wings 10, as extending outward of the body in the X-direction, are folded along the edge portions 81 of the panties 80 so that they are hooked on the panties 80 by the adhesive portions 13. With these wings 10 thus provided, it is possible to prevent the edge portions of the panties from being blotted or the sanitary napkin 1E from going out of position.

In the back sheet 3 of this sanitary napkin 1E, the two side regions 32 provide the high optical transmittance regions (b), and the central region 31 provides the high moisture-permeable region (a). When the sanitary napkin 1E is attached to the panties 80, as shown in FIG. 9, therefore, the wings 10 are so hardly prominent that the color of the panties 80 can be seen through the wings 10. This makes the sanitary napkin 1E unclear from the appearance. Here, the top sheet 4 used at this time has to be high in the optical transmittance.

As in the foregoing diaper 1A, the regions (b) are preferred to have a total optical transmittance of 60% or more according to JIS-K-7105. As in the diaper 1A, on the other hand, the moisture-permeable region (a) is preferred to have a moisture-permeability of 1,000 g/m²·24 hrs or more so as to prevent the panties from becoming stuffy in its inside while wearing the sanitary napkin 1E.

In the region (a), moreover, the total optical transmittance is preferred to be 50% or less according to JIS-K-7105 so that the absorbed mensual blood may not be seen at the back side through the body of the sanitary napkin. It is, therefore, preferable that the moisture-permeable region (a), i.e., the low optical transmittance region is positioned at least in the generally widthwise central portion of the region having the absorbent core 2 and over one half or more of the width size of the absorbent core 2, and/or in the generally longitudinal central portion of the region having the absorbent core 2 and over one half or more of the longitudinal size of the absorbent core 2.

In the region (a), the back sheet 3 is preferred to have a tearing strength of 20 g or more so that it may be prevented from being broken by the adhesion of the adhesive portion 12 when the sanitary napkin 1E is removed after use from the panties 80. In the regions (b), on the other hand, the back sheet 3 is preferred to have a tearing strength of 200 g or more so that the wings 10 may be prevented from being torn from the body.

The wings 10 are preferred to have a rigidity at some level so that they may be easily attached to the crotch portion 82 of the panties 80. Therefore, the rigidity (as measured by the cantilever method according to JIS L1096) of the regions (b) in the back sheet 3 is preferably at 30 mm or higher.

Here, the region (a) and the regions (b) are given different thicknesses so that the wings 10 are easily folded at their boundaries between the regions (a) and (b). Therefore, the sanitary napkin 1E can be easily attached because the wings 10 are easily folded along the edge portions 81 of the panties 80.

Here, the regions (b) need not be formed all over the two side regions 32 but may be provided exclusively at the portions forming the wings 10.

The back sheet 3 of the sanitary napkin 1E can be prepared in a manner similar to that used in the aforementioned diaper. For example, the central region in the widthwise direction (or the CD) of the film being fed may be exclusively embossed by using the embossing rolls 70a and 70b shown in FIG. 4A but having the corrugations of FIG. 4B at their central portions.

In the back sheet of the absorbent article of the invention, it is possible to form the high optical transmittance region in a necessary extension at a target portion. This back sheet should not be limited to the open type diaper or the sanitary napkin thus far described but could be applied to another absorbent article such as a diaper, as formed in advance into an underwear shape, a urine absorbing pad or a liner sheet.

In the absorbent article of the invention, as has been described hereinbefore, there are formed in one back sheet the high optical transmittance portion (or the region (b)) and the high air- and moisture-permeable portion (or the region (a)). In the diaper, for example, the region (b) is formed at the center so that whether or not the discharge has been made can be confirmed from the outside of the diaper being worn. In the sanitary napkin, on the other hand, the regions (b) are formed in the wings so that the presence of the wings cannot be seen from the outside of the panties. As a result, the high optical transmittance region can be formed in a portion of the absorbent article while the air-permeability and the moisture-permeability being retained in the entire absorbent article. Moreover, the strength of the back sheet is hard to degrade.

According to the invention, on the other hand, the back sheet having an optical transmittance changed partially can be manufactured at a low cost and with ease.

Here, 'comprises/comprising' when used in this specification is taken to specify the presence of stated features, integers, steps or components but does not preclude the presence or addition of one or more other features, integers, steps, components or groups thereof.

Although various exemplary embodiments have been shown and described, the invention is not limited to the embodiments shown. Therefore, the scope of the invention is intended to be limited solely by the scope of the claims that follow.

What is claimed is:

1. A sanitary napkin comprising:
   a liquid-permeable top sheet;
   a back sheet; and
   an absorbent core sandwiched between said top sheet and back sheet,
   wherein said back sheet is formed of a resin film containing an inorganic filler in a resin base material, and
   wherein said back sheet includes;
   a stretched moisture permeable region; and
   a high optical transmittance region having a lower degree of orientation than said moisture-permeable region and/or left unstretched,
   wherein said sanitary napkin includes a pair of wing portions extending outwardly from both sides of said absorbent core in the latitudinal direction,
   wherein said back sheet is divided into three regions: one moisture-permeable region located centrally of said absorbent core; and two high optical transmittance regions located on both sides of said moisture-permeable region to cover said wing portions.

2. A sanitary napkin comprising:
   a liquid-permeable top sheet;
   a back sheet; and
   an absorbent core sandwiched between said top sheet and back sheet,
   wherein said back sheet is formed of a resin film containing an inorganic filler in a resin base material, and
   wherein said back sheet includes;
   a stretched moisture-permeable region; and
   a high optical transmittance region having a lower degree of orientation than said moisture-permeable region and/or left unstretched,
   wherein said moisture-permeable region extends entirely across the absorbent core with a constant width along a longitudinal or latitudinal center thereof,
   wherein said a sanitary napkin includes a pair of wing portions extending outwardly from both sides of said absorbent core in the latitudinal direction,
   wherein said back sheet is divided into three regions; one moisture-permeable region located centrally of said absorbent core; and two high optical transmittance regions located on both sides of said moisture-permeable region to cover said wing portions.

* * * * *